(12) United States Patent
Lamoise et al.

(10) Patent No.: US 10,786,684 B2
(45) Date of Patent: Sep. 29, 2020

(54) DERMATOLOGICAL TREATMENT DEVICE PROVIDED WITH A MEANS FOR MONITORING FANS

(71) Applicant: URGO RECHERCHE INNOVATION ET DEVELOPPEMENT, Chenôve (FR)

(72) Inventors: Michel Lamoise, Bessey les Cîteaux (FR); Guirec Le Lous, Paris (FR); Jean-François Peyre, Rousset (FR)

(73) Assignee: URGO RECHERCHE INNOVATION ET DEVELOPPEMENT, Chenôve (FR)

( * ) Notice: Subject to any disclaimer, the term of this patent is extended or adjusted under 35 U.S.C. 154(b) by 79 days.

(21) Appl. No.: 16/068,204

(22) PCT Filed: Jan. 6, 2017

(86) PCT No.: PCT/EP2017/000013
§ 371 (c)(1),
(2) Date: Jul. 5, 2018

(87) PCT Pub. No.: WO2017/118606
PCT Pub. Date: Jul. 13, 2017

(65) Prior Publication Data
US 2019/0009103 A1      Jan. 10, 2019

(30) Foreign Application Priority Data

Jan. 7, 2016  (FR) ...................... 16 00035

(51) Int. Cl.
*A61N 5/06*      (2006.01)
*A61B 18/20*     (2006.01)
(Continued)

(52) U.S. Cl.
CPC ............ *A61N 5/0616* (2013.01); *A61B 18/20* (2013.01); *A61B 18/203* (2013.01);
(Continued)

(58) Field of Classification Search
CPC ........ A61B 18/203; A61B 2018/00005; A61B 2018/00017; A61B 2018/00452;
(Continued)

(56) References Cited

U.S. PATENT DOCUMENTS 6,407,672 B1    6/2002  Grenz et al.
9,393,070 B2 *  7/2016  Gelfand ............. A61B 18/1492
(Continued)

FOREIGN PATENT DOCUMENTS

GB    2421982 A       7/2006
WO    2009071592 A1   6/2009

OTHER PUBLICATIONS

Microchip, TC670 Tiny Predictive Fan Failure Detector, 2012, http://ww1.microchip.com/downloads/en/DeviceDoc/21688D.pdf (Year: 2012).*

(Continued)

*Primary Examiner* — Jonathan T Kuo
(74) *Attorney, Agent, or Firm* — Leason Ellis LLP

(57) ABSTRACT

The invention relates to a device (1) for dermatological treatment, comprising a laser head (2) suitable for directing a laser beam (3) towards a target zone (4), at least one fan (5) suitable for dissipating the heat emitted by the laser head (2), and at least one monitoring means (6) suitable for detecting a fault in at least one fan (5) and for controlling at least one means (7) for inhibiting the laser beam (3) when a fault is detected.

9 Claims, 1 Drawing Sheet

Figure 1:
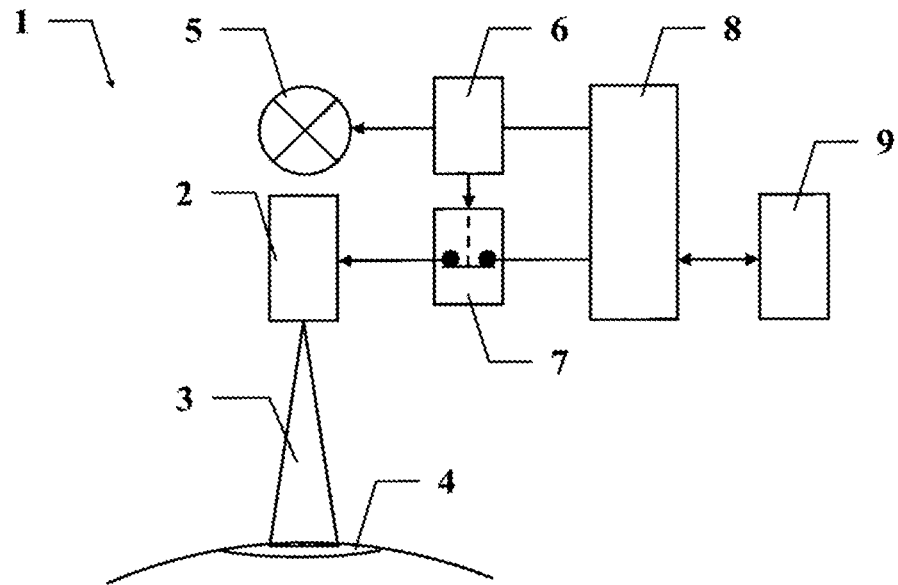

(51) Int. Cl.
*A61B 18/00* (2006.01)
*A61N 5/067* (2006.01)

(52) U.S. Cl.
CPC .............. *A61B 2018/00005* (2013.01); *A61B 2018/00017* (2013.01); *A61B 2018/0047* (2013.01); *A61B 2018/00452* (2013.01); *A61B 2018/00791* (2013.01); *A61B 2018/00892* (2013.01); *A61N 2005/067* (2013.01); *A61N 2005/0643* (2013.01); *A61N 2005/0655* (2013.01)

(58) Field of Classification Search
CPC .. A61B 2018/0047; A61B 2018/00791; A61B 2018/00892; A61B 18/20–18/28; A61N 2005/0643; A61N 2005/0655; A61N 2005/067; A61N 5/0616; A61N 5/06–2005/073; A61F 7/00–2007/126; G08B 21/00–21/0211
See application file for complete search history.

(56) References Cited

U.S. PATENT DOCUMENTS

| | | |
|---|---|---|
| 2012/0283712 A1 | 11/2012 | Youngquist et al. |
| 2013/0310823 A1* | 11/2013 | Gelfand ............ A61B 18/1492 606/33 |
| 2015/0224332 A1* | 8/2015 | Hewitson ................. A61N 5/06 607/89 |

OTHER PUBLICATIONS

International Search Report in corresponding International Patent Application No. PCT/EP2017/000013, dated Apr. 24, 2017. 3 pages.
International Preliminary Report on Patentability in corresponding International Patent Application No. PCT/EP2017/000013, dated Jul. 10, 2018. 6 pages.

* cited by examiner

DERMATOLOGICAL TREATMENT DEVICE PROVIDED WITH A MEANS FOR MONITORING FANS

CROSS-REFERENCE TO RELATED PATENT APPLICATIONS

This application is a U.S. National Stage Application under 35 U.S.C. § 371 of International Patent Application No. PCT/EP2017/000013, filed Jan. 6, 2017, which claims the benefit of priority under 35 U.S.C. Section 119(e) of French Patent Application number FR 16/00035 filed Jan. 7, 2016, all of which are incorporated by reference in their entireties. The International Application was published on Jul. 13, 2017, as International Publication No. WO 2017/118606 A1.

The present patent application claims the priority of French patent application FR 16/00035 filed on Jan. 7, 2016, which is incorporated into the present patent application by reference.

The present invention relates to a dermatological treatment device comprising a laser head able to fire a laser beam. Such a device is typically used to create precise and localized heating of a target zone, said target zone corresponding to the wound of a patient that comprises dermal tissues, in order to accelerate healing.

Such a dermatological treatment device is for example illustrated by the device described in international application WO 2009/071592 by the Applicant.

Now, although heating of the target zone is desired, this is not the case for heating of the dermatological treatment device as such. Indeed, such heating could prove detrimental both to the performance and the longevity of such a device. Therefore, and in order to limit such heating, such a dermatological treatment device is typically equipped with at least one fan, which is positioned and configured so as to dissipate the heat given off by the laser head.

This heating may clearly lead to a malfunction of the laser head if it is excessive, but not only then. Indeed, when it involves monitoring the amount of heat transmitted to the tissues, the device generally comprises a pyrometer capable of measuring the temperature of said tissues. Then, excessive heating of the laser head could detrimentally distort the temperature measured by the pyrometer and thus unfavorably affect the quantity of heat transmitted to the tissues, either causing a burn of the latter, or administering an ineffective treatment thereto.

It is therefore important to monitor all possible causes of such heating in order to prevent them.

To that end, the present invention proposes a dermatological treatment device comprising a laser head able to fire a laser beam toward a target zone, at least one fan suitable for dissipating the heat emitted by the laser head, and at least one monitoring means suitable for detecting a fault in at least one fan and controlling at least one means for inhibiting the laser beam when a fault is detected.

According to another feature, the command of the inhibiting means is persistent.

According to another feature, the monitoring means observes a signal indicative of the speed of said at least one fan and detects a fault when the speed becomes lower than a speed threshold or is canceled out.

According to another feature, the signal indicative of the speed is the command current circulating in said at least one fan.

According to another feature, the speed threshold is configurable.

According to another feature, the monitoring means is also capable of sending an alert to the operator when a fault is detected.

According to another feature, the monitoring means is cabled.

According to another feature, the monitoring means comprises at least one TC670 component, produced by MICROCHIP, preferably one such component per fan.

According to another feature, the device also comprises at least one pyrometer able to measure a temperature of the target zone as described in patent EP 2,237,731. Preferably, such a pyrometer is separated from the laser head by a thermal insulation, preferably a foam.

Figure 2:
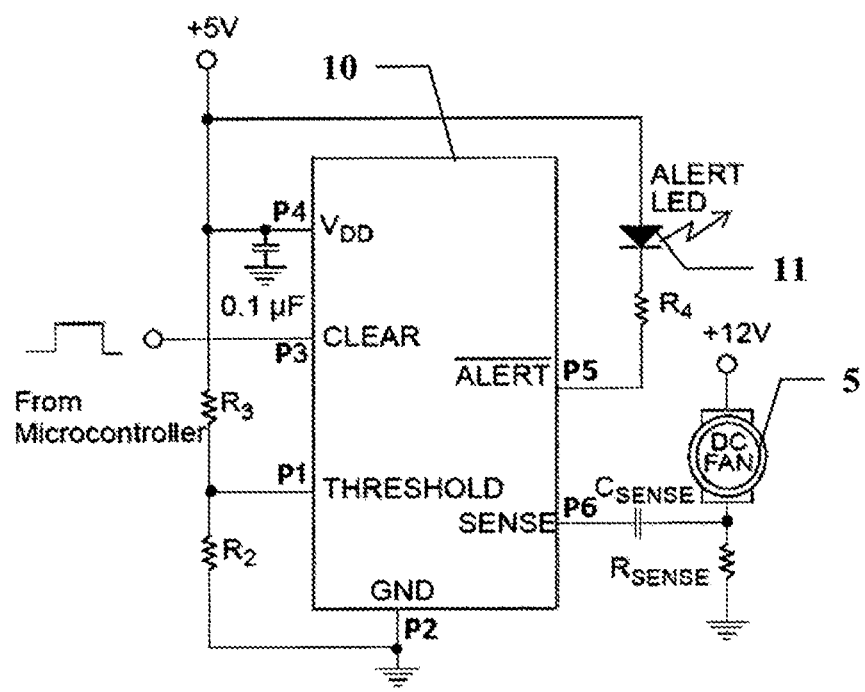

Other features, details and advantages of the invention will emerge more clearly from the detailed description provided below for information in connection with the drawings, in which:

FIG. 1 schematically shows a dermatological treatment device in its usage environment, FIG. 2 shows the cabling of a monitoring component.

As illustrated in FIG. 1, the dermatological treatment device 1 comprises a laser head 2. The laser head 2 is able to fire a laser beam 3 toward a target zone 4, located on the skin of a patient. The purpose of this illumination is to provide controlled heating of the skin at the target zone 4, this heating making it possible to encourage healing.

A command unit 8 makes it possible to control the device 1 and thus commands the laser head 2 and the fan(s) 5. A man-machine interface 9 allows an operator to communicate with the device 1 and in particular the command unit 8 in order to configure and command the device 1.

Parasitically, the operation of the laser head 2 in order to perform laser shots causes heating thereof and of the components located nearby. Therefore, at least one fan 5 is advantageously positioned so as to dissipate the heat emitted by this laser head 2.

In light of the consequences, which may be serious, of excessive heating caused by incorrect operation of at least one fan 5, monitoring of the fans 5 is particularly advantageous.

To that end, the dermatological treatment device 1 further comprises at least one monitoring means 6 suitable for detecting a fault of at least one fan 5 and commanding at least one inhibiting means 7 of the laser beam 3 when a fault is detected.

Thus, once a malfunction of at least one of said at least one fan 5 is detected, said at least one inhibiting means 7 is commanded in order to immediately stop any laser firing and any possible consequence of the laser beam 3. An inhibition of the laser beam 3 means that an in-progress shot is stopped immediately and a future shot is made impossible. A request to trigger a new shot is ineffective in that a firing request is impossible or refused.

The inhibiting means 7 can act in different ways, as long as it prevents the laser beam 3 from reaching the target zone 4. The inhibiting means 7 can be electric and/or logic-based and intervene upstream by cutting the power supply of the laser or the laser head 2, or by cutting its command. The inhibiting means 7 may further be optical in that it modifies or conceals the laser beam 3 by moving an optical lens present on the laser beam 3 or in that it inserts a concealing element in the laser beam 3, such as a screen, between the laser head 2 and the target 4.

The prohibition against a new firing may further comprise mechanical, electrical or logic blocking of a firing command means.

The inhibition of the laser beam 3 must advantageously be prolonged until the fault having caused it can be analyzed, even if the detection of the fault by the monitoring means 6 produces a sporadic signal. Therefore, according to one advantageous feature, the command of the inhibiting means 7 is persistent. The inhibiting means 7, once triggered in an inhibited state by a fault alert from the monitoring means 6, remains in this inhibited state, even if the fault alert disappears. This is done based on the technology used for the monitoring means 6 and the inhibiting means 7. Thus, this can be a memory for a computer technology, or a self-maintenance device for a relay-based technology. The device providing the persistence can be integrated into the monitoring means 6, the inhibiting means 7 or the command unit 8.

A rearming action must advantageously be done, by a qualified person, once the fault is corrected, to eliminate the inhibition and once again make it possible to perform a laser firing.

According to one feature, the monitoring means 6 observes a signal indicative of the speed of said at least one fan 5. The monitoring means 6 detects a fault when the speed becomes lower than a speed threshold or is canceled. The monitoring means 6 then emits an alert signaling said fault.

According to one possible embodiment, the signal indicative of the speed is a signal from a speed sensor driven by the fan 5.

According to another embodiment, advantageous in that it does not require a component or additional cabling, the signal indicative of the speed does not require a component or additional cabling, the signal indicative of the speed is the command current circulating in said at least one fan 5. Due to the type of motor used by the fans 5, the command current of a fan 5 is representative of the speed actually reached by the fan 5. Therefore, observing this current makes it possible to obtain an estimate of the speed of the fan 5.

According to another feature, the speed threshold is advantageously configurable. This advantageously makes it possible to place such a speed threshold below the minimum speed generally adopted by the fan 5. Thus, if the actual speed of the fan 5 drops below this speed threshold, it is certain or at least highly likely that the fan will have a fault.

A nil speed or a stopped fan, irrespective of the reason, is a particular case of an excessively low speed, optionally detectable by means other than observing the speed.

The first function of the monitoring means 6 is, when it detects a fault, to send an alert, through any means, to the attention of an inhibiting means 7 in order to command a passage of the latter to an inhibited state. In addition to this main function, the monitoring means 6 may further advantageously, directly or via at least one intermediate means, send an alert to the operator in order to inform him that a fault has been detected. This alert may be sent through any means and in different ways. It may involve a visible or audible warning. It may further involve information sent to a man-machine interface 9 so that the latter displays the alert to the attention of the operator. Such an alert transmission is useful in that it allows the operator to understand why the laser beam is inhibited, either that the firing in progress has stopped, or that an attempt to begin a firing has not been followed by any effect.

The monitoring means 6 has been described functionally. It may be done by any means and according to any technique able to carry out the described functions. However, regarding a safety function, influencing a safe use of the treatment device 1, a cabled embodiment is advantageously preferred, using an electrical and/or electronic circuit in order to offer better reliability. According to this feature, the use, even partially, of computer technology is thus preferably avoided.

According to one embodiment, the monitoring means 6 can be built around a dedicated component, suitable for this monitoring function of a current indicative of a speed. Such a component is for example a TC670 reference component, as produced by the company MICROCHIP.

Such a component 10 is shown in FIG. 2 in an illustrative environment. This component 10 comprises 6 pins P1-P6. P4 receives a supply voltage Vdd, here +5V, and P2 is connected to a voltage reference GND. In connection with a fan 5 functionally cabled between a supply voltage +12V and a voltage reference, a voltage image of the current flowing in the fan 5 is produced using a capacitor Csense. This image voltage of the current is transmitted to the component 10 via its pin P5/SENSE. The component 10 analyzes this voltage SENSE in order to detect a low speed, below a speed threshold. When such a fault condition appears, the component 10 changes the status of the output signal ALERT present on the pin P5. This signal goes from a high state to a low state in the presence of a fault, in order to be "failsafe". Here in an illustrative manner, this signal illuminates an LED 11/ALERT LED. The component 10 performs the persistence function, in that the fault/alert state is maintained following a fault detection. The pin P3/CLEAR, however, makes it possible to rearm and here is for example connected to an output of a microcontroller, such as a microcontroller contained in the control unit 8. A pin P1/THRESHOLD makes it possible to enter a speed threshold setpoint, using a voltage proportional to the supply voltage Vdd. Here, this is for example done using the divider bridge R2/R3, the relative resistance values of which determine the speed threshold.

Such a component 10 is preferably used to monitor a fan 5. One then preferably uses one such component 10 per fan 5.

As described, the invention aims to maintain a moderate temperature at the laser head 2 in order to guarantee safe and correct operation of the device 1.

However, the measurements done are not certain to guarantee the result. It is in fact possible for the laser head 2 to reach higher temperatures despite everything. This is particularly detrimental for a pyrometer potentially present in the device 1, most often near the laser head 2. Therefore, and as an additional measure making it possible to achieve the same result, the pyrometer is advantageously separated from the laser head 2 by a thermal insulator, preferably a foam.

The invention claimed is:

1. A dermatological treatment device comprising a laser head able to fire a laser beam toward a target zone and at least one fan suitable for dissipating the heat emitted by the laser head, characterized in that it further comprises at least one monitoring means suitable for detecting a fault in the at least one fan, controlling at least one means for inhibiting the laser beam when the fault is detected, and sending an alert to an operator in order to inform the operator that the fault has been detected, and at least one contactless pyrometer able to measure a temperature of the target zone, where the pyrometer is separated from the laser head by a thermal insulation, where the thermal insulation is a foam.

2. The device according to claim 1, where a command of at least one means for inhibiting is persistent.

3. The device according to claim 1, where said at least one monitoring means observes a signal indicative of a speed of said at least one fan and detects the fault when the speed becomes lower than a speed threshold or is canceled out.

4. The device according to claim 3, where the signal indicative of the speed is a command current circulating in said at least one fan.

5. The device according to claim 1, comprises a configuring means suitable for allowing a configuration of a speed threshold of the at least one fan.

6. The device according to claim 1, where said at least one monitoring means further comprises an alert means suitable for sending an alert to the operator when the fault is detected.

7. The device according to claim 1, where the at least one monitoring means is cabled.

8. The device according to claim 1, where said at least one monitoring means comprises at least one TC670 component, produced by MICROCHIP.

9. The device according to claim 8, where said at least one monitoring means comprises one TC670 component, as produced by MICROCHIP per fan.

* * * * *